(12) United States Patent
Clark

(10) Patent No.: US 7,884,269 B2
(45) Date of Patent: Feb. 8, 2011

(54) BARLEY CULTIVAR CHAMPION

(75) Inventor: Dale R Clark, Bozeman, MT (US)

(73) Assignee: Monsanto Technology, LLC, St. Louis, MO (US)

( * ) Notice: Subject to any disclaimer, the term of this patent is extended or adjusted under 35 U.S.C. 154(b) by 241 days.

(21) Appl. No.: 12/210,367

(22) Filed: Sep. 15, 2008

(65) Prior Publication Data

US 2010/0071082 A1    Mar. 18, 2010

(51) Int. Cl.
*A01H 5/10* (2006.01)
*A01H 5/00* (2006.01)
*A01H 1/00* (2006.01)
*C12N 5/04* (2006.01)
*C12N 15/82* (2006.01)

(52) U.S. Cl. .................. 800/320; 435/410; 435/430; 800/266; 800/298; 800/300; 800/301; 800/302

(58) Field of Classification Search ................. None
See application file for complete search history.

(56) References Cited

U.S. PATENT DOCUMENTS

| | | | |
|---|---|---|---|
| 5,304,719 | A | 4/1994 | Segebart |
| 5,367,109 | A | 11/1994 | Segebart |
| 5,523,520 | A | 6/1996 | Hunsperger et al. |
| 5,763,755 | A | 6/1998 | Carlone |
| 5,850,009 | A | 12/1998 | Kevern |

OTHER PUBLICATIONS

Eshed, et al., 1996. Less-than-additive epistatic interactions of quantitative trait loci in tomato. Genetics 143:1807-1817.

Kraft, et al., 2000. Linkage disequilibrium and fingerprinting in sugar beet. Theor. App. Genet. 101:323-326.

PVP 9300211 BARLEY 'Baronesse'.

US PVP Certificate No. 200800382, Granted Application of WestBred, LLC, Jun. 3, 2009.

US PVP Certificate No. 9300211, Granted Application of Peterson Seed Company, Inc., May 31, 1996.

Canadian PBR Certificate 3276, Granted Application of Monsanto Technology LLC, Aug. 28, 2008.

*Primary Examiner*—Ashwin Mehta
(74) *Attorney, Agent, or Firm*—Jondle & Associates, P.C.

(57) ABSTRACT

A barley cultivar, designated Champion, is disclosed. The invention relates to the seeds of barley cultivar Champion, to the plants of barley Champion, and to methods for producing a barley plant produced by crossing barley cultivar Champion with itself or another barley variety. The invention also relates to methods for producing a barley plant containing in its genetic material one or more transgenes and to the transgenic barley plants and plant parts produced by those methods. The invention also relates to barley varieties or breeding varieties and plant parts derived from barley cultivar Champion, to methods for producing other barley varieties, lines or plant parts derived from barley cultivar Champion, and to the barley plants, varieties, and their parts derived from the use of those methods. The invention further relates to hybrid barley seeds and plants produced by crossing barley cultivar Champion with another barley cultivar. This invention further relates to methods for developing other barley varieties or breeding lines derived from variety Champion including cell and tissue culture, haploid systems, mutagenesis, and transgenic derived lines.

22 Claims, No Drawings

BARLEY CULTIVAR CHAMPION

BACKGROUND OF THE INVENTION

The present invention relates to a new and distinctive barley cultivar designated Champion. All publications cited in this application are herein incorporated by reference.

Barley (*Hordeum vulgare* L.) is a grain that is grown worldwide with three main market classes, malt, feed and food. Most of the barley grain produced in the United States is used as an ingredient in cattle, pig, or poultry feed. Another major use for barley is malt production. Malt is used in the brewing and distilling industries to produce alcoholic beverages. Barley varieties that are preferred for producing malt are selected on the basis of characteristics such as kernel plumpness, low protein content and low Beta-glucan content. Barley grain that has more than about 13.5 weight percent protein on a dry basis or is too dark in color is rejected by malting plants. Significant overlap between the classes can occur since barley that does not meet malting specifications can be used for feed, food and potentially the emerging biofuels industry.

Barley is a nutritious food ingredient for humans or household pets. When used as a food ingredient, for malting or feed, barley grain that has a cemented hull (referred to as covered) must be processed to remove that hull. A commonly used processing step known as pearling removes the hull and a substantial portion of the bran and the germ to produce a pearled barley grain, such that at least about 15 to about 40 weight percent of the outer grain is removed. Some barley varieties developed especially for food are hulless, i.e., they have a loose hull so do not have to be pearled prior to consumption. Hulless barley must be cleaned as do all grains prior to entering the human food markets, but loose hulls can be removed easily with only slight modifications to the cleaning plants. Food ingredient manufacturers may grind the cleaned barley to produce flour or roll the barley to produce flakes. Food ingredient manufacturers may also utilize the cleaned barley as a whole berry (seed).

Barley consumed as food in Japan is typically mixed with rice. Japanese consumers have a preference for white rice, thus, it is desirable to process barley to look similar to rice. Barley processing in Japan involves pearling the outer layers to achieve the bright, white color and splitting the grain in half to be similar in size as rice. Japanese barley processors prefer barley that has a cemented hull (covered) and that has little cracking during the pearling process.

Waxy barley is a naturally occurring variant that has recently been investigated for potential in food and industrial processing. Barley lines having the waxy phenotype have reduced amounts of amylose starch in the seed. The waxy trait may be useful in the production of high maltose syrup from barley (U.S. Pat. No. 4,116,770, Goering 1978) and in the production of flour and flakes (U.S. Pat. Nos. 5,614,242, Fox 1997 and 6,238,719, Fox, 2001) that have health benefits.

The health promoting benefits of barley consumption have been investigated in human clinical trials. Studies have shown that individuals consuming barley that contains Beta-glucan soluble fiber have significant reductions in total and LDL plasma cholesterol (Behall et al. 2004. Am. J. Clin. Nutr. 80:1185-1193; Behall et al. 2004. J. Amer. Coll. Nutr. 23:55-62) as well as blood pressure (Hallfrisch et al. 2003. Cer. Chem. 80:80-83; Behall et al. 2006. Nutrition. Res. 26:644-650). In May 2006, the FDA granted a petition to allow foods containing barley with 0.75 g of Beta-glucan to carry a health claim "barley lowers cholesterol when consumed as part of a healthy diet" (Federal Register 71 (98):29248-29250).

Cultivated barley is a naturally self-fertilizing species, although there is a small percentage of cross-fertilization. Natural genetic and cytoplasmic male sterility is available to use in breeding and in hybrid seed production. Using all of the tools available to a breeder, it is possible to develop pure lines that are uniform in growth habit, maturity, yield, and other qualitative and quantitative characteristics. These lines can be released as inbred varieties, as inbreds for hybrid barley, or as lines to be further manipulated in the development of new lines or varieties or that incorporate proprietary genetic material.

Barley varieties may differ from each other in one or more traits and can be classified and differentiated according to the specific traits they possess. For example, there are types of barley known as two-rowed and other types known as six-rowed, referring to the number and positioning of kernels on the spike. Barley lines also can be classified as spring barley or winter barley, referring to the growth habit, or by the adherence of hulls on the seed, or by the type of starch in the seed. There are, of course, many other traits which differentiate the various lines. A discussion of breeding methods for developing barley lines and of some traits in barley can be found in Foster, A. E., Barley, pp. 83-125, and in Fehr, W. R., ed., *Principles of Cultivar Development* Vol. 2 Crop species. Macmillan, N.Y. (1987). Once a breeder has developed a pure line, it may be given a unique name and released as a cultivar under that name. While named cultivars are not necessarily pure lines (they could be a mixture of genotypes or even be a hybrid) presently, most named barley cultivars are pure lines.

The present invention relates to a new and distinctive barley variety, designated Champion, which has been the result of years of careful breeding and selection as part of a barley breeding program. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, tolerance to drought and heat, better agronomic qualities and improved grain quality.

Field crops are bred through techniques that take advantage of the plant's method of pollination. A plant is self-pollinated if pollen from one flower is transferred to the same or another flower of the same plant. A plant is sib-pollinated when individuals within the same family or line are used for pollination. A plant is cross-pollinated if the pollen comes from a flower on a different plant from a different family or line. The term cross-pollination herein does not include self-pollination or sib-pollination.

A cross between two different homozygous lines produces a uniform population of hybrid plants that may be heterozygous for many gene loci. A cross of two heterozygous plants each that differ at a number of gene loci will produce a population of plants that differ genetically and will not be uniform. Regardless of parentage, plants that have been self-pollinated and selected for type for many generations become homozygous at almost all gene loci and produce a uniform population of true breeding progeny. The term "homozygous plant" is hereby defined as a plant with homozygous genes at 95% or more of its loci. The term "inbred" as used herein refers to a homozygous plant or a collection of homozygous plants.

Choice of breeding or selection methods depends on the mode of plant reproduction, the heritability of the trait(s) being improved, and the type of variety used commercially (e.g., $F_1$ hybrid variety, pureline variety, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination and the number of hybrid offspring from each successful cross.

Pedigree breeding is commonly used for the improvement of self-pollinating crops. Two parents that possess favorable, complementary traits are crossed to produce an $F_1$. An $F_2$ population is produced by selfing or sibbing one or several $F_1$s. Selection of the best individuals may begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_5$, $F_6$ and $F_7$), the best lines or mixtures of phenotypically similar lines are tested for potential release as new varieties.

Backcross breeding has been used to transfer genes for simply inherited, qualitative, traits from a donor parent into a desirable homozygous variety that is utilized as the recurrent parent. The source of the traits to be transferred is called the donor parent. After the initial cross, individuals possessing the desired trait or traits of the donor parent are selected and then repeatedly crossed (backcrossed) to the recurrent parent. The resulting plant is expected to have the attributes of the recurrent parent (e.g., variety) plus the desirable trait or traits transferred from the donor parent. This approach has been used extensively for breeding disease resistant varieties.

Each barley breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful varieties produced per unit of input (e.g., per year, per dollar expended, etc.).

Various recurrent selection techniques are used to improve quantitatively inherited traits controlled by numerous genes. The use of recurrent selection in self-pollinating crops depends on the ease of pollination and the number of hybrid offspring from each successful cross. Recurrent selection can be used to improve populations of either self- or cross-pollinated crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued. Plants from the populations can be selected and selfed to create new varieties.

Another breeding method is single-seed descent. This procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed. In a multiple-seed procedure, barley breeders commonly harvest one or more spikes (heads) from each plant in a population and thresh them together to form a bulk. Part of the bulk is used to plant the next generation and part is put in reserve. The procedure has been referred to as modified single-seed descent. The multiple-seed procedure has been used to save labor at harvest. It is considerably faster to thresh spikes with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Bulk breeding can also be used. In the bulk breeding method an $F_2$ population is grown. The seed from the populations is harvested in bulk and a sample of the seed is used to make a planting the next season. This cycle can be repeated several times. In general when individual plants are expected to have a high degree of homozygosity, individual plants are selected, tested, and increased for possible use as a variety.

Molecular markers including techniques such as Starch Gel Electrophoresis, Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs), and Single Nucleotide Polymorphisms (SNPs) may be used in plant breeding methods. One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the markers of the donor parent. Using this procedure can minimize the amount of genome from the donor parent that remains in the selected plants. It can also be used to reduce the number of crosses back to the recurrent parent needed in a backcrossing program (Openshaw et al. Marker-assisted Selection in Backcross Breeding. *In: Proceedings Symposium of the Analysis of Molecular Marker Data*, 5-6 Aug. 1994, pp. 41-43. Crop Science Society of America, Corvallis, Oreg.). The use of molecular markers in the selection process is often called Genetic Marker Enhanced Selection.

The production of double haploids can also be used for the development of homozygous lines in the breeding program. Double haploids are produced by the doubling of a set of chromosomes (1N) from a heterozygous plant to produce a completely homozygous individual. This can be advantageous because the process omits the generations of selfing needed to obtain a homozygous plant from a heterozygous source. Various methodologies of making double haploid plants in barley have been developed (Laurie, D. A. and S. Reymondie, *Plant Breeding*, 1991, v. 106:182-189. Singh, N. et al., *Cereal Research Communications*, 2001, v. 29:289-296; Redha, A. et al., *Plant Cell Tissue and Organ Culture*, 2000, v. 63:167-172; U.S. Pat. No. 6,362,393)

Though pure-line varieties are the predominate form of barley grown for commercial barley production hybrid barley is also used. Hybrid barleys are produced with the help of cytoplasmic male sterility, nuclear genetic male sterility, or chemicals. Various combinations of these three male sterility systems have been used in the production of hybrid barley.

Descriptions of other breeding methods that are commonly used for different traits and crops can be found in one of several reference books (e.g., Allard, Principles of Plant Breeding, 1960; Simmonds, *Principles of Crop Improvement*, 1979).

Promising advanced breeding lines are thoroughly tested and compared to appropriate standards in environments representative of the commercial target area(s). The best lines are candidates for new commercial varieties; those still deficient in a few traits may be used as parents to produce new populations for further selection.

A most difficult task is the identification of individuals that are genetically superior, because for most traits the true genotypic value is masked by other confounding plant traits or environmental factors. One method of identifying a superior genotype is to observe its performance relative to other experimental genotypes and to a widely grown standard variety. Generally a single observation is inconclusive, so replicated observations are required to provide a better estimate of its genetic worth.

A breeder uses various methods to help determine which plants should be selected from the segregating populations and ultimately which lines will be used for commercialization. In addition to the knowledge of the germplasm and other skills the breeder uses, a part of the selection process is dependent on experimental design coupled with the use of statistical analysis. Experimental design and statistical analysis are used to help determine which plants, which family of plants, and finally which lines are significantly better or different for one or more traits of interest. Experimental design methods are used to control error so that differences between two lines can be more accurately determined. Statistical analysis includes the calculation of mean values, determination of the statistical significance of the sources of variation, and the calculation of the appropriate variance components. Five and one percent significance levels are customarily used to determine whether a difference that occurs for a given trait is real or due to the environment or experimental error.

Plant breeding is the genetic manipulation of plants. The goal of barley breeding is to develop new, unique and superior barley varieties. In practical application of a barley breeding program, the breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop exactly the same line.

Each year, the plant breeder selects the germplasm to advance to the next generation. This germplasm is grown under unique and different geographical, climatic and soil conditions, and further selections are then made during and at the end of the growing season.

Proper testing should detect major faults and establish the level of superiority or improvement over current varieties. In addition to showing superior performance, there must be a demand for a new variety. The new variety must be compatible with industry standards, or must create a new market. The introduction of a new variety may incur additional costs to the seed producer, the grower, processor and consumer, for special advertising and marketing, altered seed and commercial production practices, and new product utilization. The testing preceding release of a new variety should take into consideration research and development costs as well as technical superiority of the final variety. It must also be feasible to produce seed easily and economically.

These processes, which lead to the final step of marketing and distribution, can take from six to twelve years from the time the first cross is made. Therefore, development of new varieties is a time-consuming process that requires precise forward planning, efficient use of resources, and a minimum of changes in direction.

Barley (*Hordeum vulgare* L.), is an important and valuable field crop. Thus, a continuing goal of barley breeders is to develop stable, high yielding barley varieties that are agronomically sound and have good grain quality for its intended use. To accomplish this goal, the barley breeder must select and develop barley plants that have the traits that result in superior varieties.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools, and methods which are meant to be exemplary and illustrative, not limiting in scope. In various embodiments, one or more of the above-described problems have been reduced or eliminated, while other embodiments are directed to other improvements.

According to the invention, there is provided a new barley cultivar designated Champion. This invention thus relates to the seeds of barley cultivar Champion, to the plants of barley cultivar Champion and to methods for producing a barley plant produced by crossing the barley cultivar Champion with itself or another barley cultivar, and the creation of variants by mutagenesis or transformation of barley cultivar Champion.

Thus, any such methods using the barley cultivar Champion are part of this invention: selfing, backcrosses, hybrid production, crosses to populations, and the like. All plants produced using barley cultivar Champion as at least one parent are within the scope of this invention. Advantageously, the barley cultivar could be used in crosses with other, different, barley plants to produce first generation ($F_1$) barley hybrid seeds and plants with superior characteristics.

In another aspect, the present invention provides for single or multiple gene converted plants of barley cultivar Champion. The transferred gene(s) may preferably be a dominant or recessive allele. Preferably, the transferred gene(s) will confer such traits as herbicide resistance, insect resistance, resistance for bacterial, fungal, or viral disease, male fertility, male sterility, enhanced nutritional quality, modified fatty acid metabolism, modified carbohydrate metabolism, modified seed yield, modified protein percent, modified beta-glucan percent, modified lodging resistance, modified lipoxygenase, beta-glucanase and/or polyphenol oxidase content and/or activity, and industrial usage. The gene may be a naturally occurring barley gene or a transgene introduced through genetic engineering techniques.

In another aspect, the present invention provides regenerable cells for use in tissue culture of barley plant Champion. The tissue culture will preferably be capable of regenerating plants having essentially all the physiological and morphological characteristics of the foregoing barley plant, and of regenerating plants having substantially the same genotype as the foregoing barley plant. Preferably, the regenerable cells in such tissue cultures will be head, awn, leaf, pollen, embryo, cotyledon, hypocotyl, seed, spike, pericarp, meristematic cell, protoplast, root, root tip, pistil, anther, floret, shoot, stem and callus. Still further, the present invention provides barley plants regenerated from the tissue cultures of the invention.

In addition to the exemplary aspects and embodiments described above, further aspects and embodiments will become apparent by study of the following descriptions.

Definitions

In the description and tables that follow, a number of terms are used. In order to provide a clear and consistent understanding of the specification and claims, including the scope to be given such terms, the following definitions are provided:

Allele. An allele is any of one or more alternative forms of a gene which relate to one trait or characteristic. In a diploid cell or organism, the two alleles of a given gene occupy corresponding loci on a pair of homologous chromosomes.

Awn. Awn is intended to mean the elongated needle-like appendages on the flower- and seed-bearing "head" at the top of the barley plant. These awns are attached to the lemmas. Lemmas enclose the stamen and the stigma as part of the florets. These florets are grouped in spikelets, which in turn together comprise the head or spike.

Backcrossing. Backcrossing is a process in which a breeder repeatedly crosses hybrid progeny back to one of the parents, for example, a first generation hybrid $F_1$ with one of the parental genotypes of the $F_1$ hybrid.

Barley Yellow Dwarf Virus: Barley yellow dwarf virus is a viral disease transmitted by aphids. The symptoms include yellow chlorosis of the older leaves, stunting, sterility and reduced kernel size.

Beta-Glucan Fiber. Beta-glucan fiber is a nonstarch polysaccharide in which individual glucose molecules (20,000-1,000,000) are linked by beta 1-4 and beta 1-3 linkages. Beta-glucan is soluble in warm water (40-45 degrees Centigrade); cellulose is insoluble in water. Beta-glucan is the main structural material in the cell walls of barley and oat grain.

Beta-Glucan Fiber Viscosity. Beta-glucan fiber viscosity describes the friction that is created in a solution by the presence of beta-glucan chains (fibers) and is measured in centipoise units.

Centipoise Units (cps). Centipoise units (cps) are the units commonly used to measure viscosity. By definition the fundamental unit of viscosity measurement is the "Poise", which is a material requiring a sheer stress of one dyne per square centimeter to produce a sheer of one inverse second, which has a viscosity of one poise or 100 centipoise.

Covered Seed. Barley seed can have a cutin layer which cements the hull (lemma and palea or glumes) to the seed. This trait is controlled by the Nud locus on chromosome 1 (7H). The homozygous dominant Nud Nud genotype results in the presence of cutin and is referred to as covered. The hull can only be removed by abrasive processing prior to consumption, known as pearling.

Deficiens. Two-row barley heads have lateral florets that do not produce seed. These lateral florets can vary in size and ability to produce pollen. Lateral florets that are very reduced in size (almost nonexistent) and never produce pollen are called deficiens.

Essentially all of the physiological and morphological characteristics. A plant having essentially all of the physiological and morphological characteristics means a plant having the physiological and morphological characteristics of the recurrent parent, except for the characteristics derived from the converted trait.

Foliar disease: Foliar disease is a general term for fungal disease which causes yellowing or browning or premature drying of the leaves. The disease typically involves *Septoria*, net blotch, spot blotch or scald.

Head. As used herein, the term "head" refers to a group of spikelets at the top of one plant stem. The term "spike" also refers to the head of a barley plant located at the top of one plant stem.

Hulless Seed. Barley seed can have a cutin layer which cements the hull (lemma and palea or glumes) to the seed. This trait is controlled by the Nud locus on chromosome 1 (7H). The homozygous recessive nud nud genotype results in the absence of cutin and is referred to as hulless. The loose hull can be easily removed at harvest or by minimal cleaning/processing prior to consumption. This has also been referred to as naked or nude seed.

Iodine Stain—IKI—Iodine/Potassium Iodide Stock Solution for Starch Test. The stock solution of iodine stain for the starch test consists of 35 g of KI (potassium iodide) and 5 g of I (Iodine) in 500 ml of distilled water. The working solution consists of a 1:3 dilution of the stock with distilled water (1:3=one part stock and two parts water).

Iodine or Starch Test. The iodine or starch test tests for the absence or reduced levels of amylose in a plant part, most often the seed. The absence or reduced levels of amylose can be detected by cutting the nonembryo end of the seed at the dough stage and staining with a dilute iodine (IKI) stain. Amylose stains blue while amylopectin stains brown.

Lodging. As used herein, the term "lodging" refers to the bending or breakage of the plant stem, or the tilting over of the plant, which complicates harvest and can diminish the value of the harvested product.

Leaf Rust: A fungal disease that results in orange-red pustules on the leaf surface. Caused by *Puccinia hordei*.

Net blotch: Net blotch refers to a fungal disease which appears as elongated black lesions running parallel to the leaf veins with distinctive, dark brown net-like patterns. Net blotch is caused by *Pyrenophora teres*.

Plant Height (Hgt): As used herein, the term "plant height" is defined as the average height in inches or centimeters of a group of plants, as measured from the ground level to the tip of the head, excluding awns.

Pearling: The process through which the outer fibrous layers of a seed are sequentially removed by abrasion. Pearling can be achieved by physical abrasion of the seed against a hard material (stone) or by the force of seed rubbing against seed at a high speed.

Powdery Mildew: Powdery mildew refers to a fungal disease that results in white to gray powdery pustules on the leaf blade with associated yellowing and browning. Powdery mildew is caused by *Blumeria graminis* f. sp. hordei.

Scab: Scab refers to a fungal disease that causes salmon-orange spore masses at the base of the glumes and on the seed. It may also cause shriveling of seed. Scab is caused by *Fusarium graminearum*.

Scald: Scald refers to a fungal disease that causes spots to develop on the leaves during cool, wet weather. The spots are oval shaped and the margins of the spots change from bluish-green to zonated brown or tan rings with bleached straw-colored centers. Scald is caused by *Rhynchosporium secalis*.

Septoria: *Septoria* refers to a fungal disease that appears as elongated, light brown spots on the leaves. It is caused by *Septoria passerinii*.

Single Gene Converted (Conversion). Single gene converted (conversion) plants refers to plants which are developed by a plant breeding technique called backcrossing wherein essentially all of the desired morphological and physiological characteristics of a variety are recovered in addition to the single gene transferred into the variety via the backcrossing technique or via genetic engineering.

Smut, covered: Covered smut refers to a fungal disease in which masses of black spores replace the seed kernels on the head. A persistent membrane can be ruptured during harvest to disperse spores. Covered smut is caused by *Ustilago hordei*.

Smut, loose: Loose smut refers to a fungal disease in which masses of black spores replace the seed kernels on the head. The thin membrane that covers the spores is easily ruptured and spores disbursed by wind. Loose smut is caused by *Ustilago nuda*.

Snot blotch: Spot blotch refers to a fungal disease that appears as dark, chocolate-colored blotches forming irregular dead patches on the leaves. Spot blotch is caused by *Cochliobolus sativus*.

Stem rust: Stem rust refers to a fungal disease that produces masses of brick-red pustules on stems and leaf sheaths. Stem rust can be caused by either *Puccinia graminis* f. sp. *tritici* or *Puccinia graminis* f. sp. *secalis*.

Stripe Rust: Stripe rust refers to a fungal disease that results in light yellowish orange pustules arranged in stripes between the veins of the leaves. Stripe rust is caused by *Puccinia strilformis* f sp. *hordei*.

Waxy Bloom: A waxy or powdery whitish to bluish coating that can be found on the surface of stems, leaves and the spike. The presence or absence of the wax is controlled genetically by a number of genes. Plant parts which do not have wax are referred to as "glossy". A synonym for presence of the wax is "glaucous".

Waxy Seed. The endosperm of waxy seed contains waxy starch granules with low amylose content. The lower amylose results in seed having an opaque appearance and can be confirmed as waxy using the Iodine test.

Waxy Starch. Starch in grain is stored in granules which can be made of varying amounts of amylopectin (branched) and amylose (straight chained) starch. Waxy starch in barley has low amylose content ranging from 0 to 20%. Amylose content in the starch granules is genetically controlled by one or more alleles at the Wax locus on chromosome 1 (7H) which encodes the production of granule-bound starch synthase. The homozygous recessive wax wax genotype has starch granules with low amounts of amylose.

DETAILED DESCRIPTION OF THE INVENTION

The variety of the invention has shown uniformity and stability for all traits, as described in the following variety description information. It has been self-pollinated a sufficient number of generations, with careful attention to uniformity of plant type to ensure homozygosity and phenotypic stability. The line has been increased with continued observation for uniformity. No variant traits have been observed or are expected in Champion, as described in Table 1 (Variety Description Information).

Champion is a normal starch, covered feed barley that originated from the cross "Baronesse"/"Camas". Baronesse is a covered feed barley developed in Germany but successfully grown in the western U.S. Camas is a covered feed barley released by the Idaho Agricultural Experiment Station. The $F_1$ was grown near Yuma, Ariz. in 1997 and the $F_2$ through $F_4$ seed generations planted near Bozeman, Mont. in the spring of 1998 through 2000. Single spikes were selected in each generation and planted as individual rows. Single spikes were selected from the $F_4$ rows and planted as single $F_5$ rows near Yuma, Ariz. in November, 2000. Agronomically acceptable (proper plant height, straw strength and disease tolerant) rows were selected, harvested and given experimental numbers. One such row was given the designation "YU501-385". The $F_6$ seed from this row was used to plant a single 5 ft.×15 ft. plot near Bozeman, Mont. and one near Calgary, Alberta, Canada. The $F_7$ seed from the Bozeman plot was harvested in September, 2001 and used to plant replicated yield trials near Bozeman, Mont. and three locations in Alberta in May, 2002. Continued yield testing of the $F_8$ to $F_{11}$ generations was performed in 2003-2006 in the states of Washington, Idaho, and Montana using the experimental designation of YU501-385 and the provinces of Alberta, Saskatchewan and Manitoba, Canada using the experimental designation of 'TR04-719'. Heads were selected for purification from an $F_9$ plot in September, 2004 and planted as head-row plots near Yuma, Ariz. in November, 2004. Uniform appearing plots were harvested individually in April, 2005 and planted separately as strips in May near Bozeman, Mont. Uniform appearing strips were harvested individually in September, 2005. Seed from these strips were planted separately near Bozeman, Mont. and near Calgary, Alberta, Canada in April, 2006. Uniform strips were harvested and bulked in August, 2006 and YU501-385 (TR04-719) was named Champion.

Champion is a 2-rowed, medium-maturing, medium-height cultivar adapted to Montana, Idaho, Washington, and Oregon. The characteristics of Champion are listed in Table 1. Comparisons between Champion and other covered barley are in Tables 2 to 5.

Champion has slightly waxy, glabrous leaves, erect juvenile growth habit, and an upright flag leaf. The stem is white, closed collared with a straight neck. The 2-rowed head is slightly waxy, tapering, erect but not dense, with rachis pubescence and is erect at maturity. The glumes are mid-sized, slightly waxy, and pubescent with mid-length rough glume awns. The lemma awns are long and rough and anthocyanin is present in the lemma awn tips. The lateral, sterile florets are greatly reduced (deficiens). The seed is covered, plump, mid-long to long in length, and white in color.

TABLE 1

VARIETY DESCRIPTION INFORMATION

| Plant: | Growth Habit: Spring |
| --- | --- |
| | Spike: Two-row |
| | Juvenile Growth Habit: Erect |
| | Plant Tillering: Intermediate |

TABLE 1-continued

VARIETY DESCRIPTION INFORMATION

|  |  |
|---|---|
|  | Maturity (50% flowering): Medium; averages 63 days after planting, similar to the variety Baronesse |
|  | Plant Height: Medium; averages 78 centimeters; 8 cm taller than the variety Baronesse |
|  | Stem Color at Maturity: White |
|  | Stem Strength: Moderately strong |
|  | Neck Shape: Straight |
|  | Collar Shape: Closed |
| Leaves: | Coleoptile Color: Green |
|  | Basal Leaf Sheath Pubescence at Seedling Stage: Absent |
|  | Basal Leaf Sheath Color: White |
|  | Leaf Color at Boot: Green |
|  | Flag Leaf at Boot: Erect, Twisted, Some Waxy Bloom |
|  | Pubescence on Leaf (first leaf below flag leaf) Blade: Very sparse |
|  | Pubescence on Leaf (first leaf below flag leaf) Sheath: Very sparse |
|  | Auricle Color: White |
|  | Pubescence on Auricle: Very sparse |
| Spike: | Exsertion: Intermediate |
|  | Shape: Tapering |
|  | Density: Erect Not Dense |
|  | Position at Maturity: Erect |
|  | Length of Spike: Long |
|  | Waxy Bloom: Slightly waxy |
|  | Hairiness of Rachis Edge: Covered |
|  | Rachilla Hairs: Long |
|  | Lateral Florets: Reduced (deficiens) |
| Awns: | Awns: Straight |
|  | Length: Long |
|  | Surface: Rough |
| Glumes: | Length: One-half of lemma |
|  | Hairiness: Completely covered |
|  | Length of Hairs: Short |
|  | Glume Awn Surface: Rough |
|  | Glume Awn Length Relative to Glume Length: Equal |
| Hull/Kernel: | Hull Type (Lemma/Palea Adherence): Covered |
|  | Wrinkling of Hull: Wrinkled |
|  | Hairs on Ventral Furrow: Present |
|  | Shape of Base: Depression |
|  | Kernel Aleurone Color: Colorless |
|  | Kernel Length: Mid-long to long |
|  | Average 1,000 Kernel Weight: 51 g, 2 g higher than Baronesse |
| Diseases: | Net blotch: Resistant |
|  | Stripe rust: Susceptible |
|  | Scald: Susceptible |
|  | Stem Rust, *Septoria*, and Spot blotch: Not Tested |
|  | Smut, loose and covered: Not Tested |
| Other Characteristics: | Champion has normal non-waxy seed (25% amylose) which stains blue when the seed is cut in half at dough stage and the iodine or starch test is performed. |

Barley cultivar Champion is similar to the parent, Baronesse. However, selection for agronomic performance resulted in Champion plants that produce higher yield and higher test weight grain than Baronesse. In addition, the head of Champion is tapering while the head of Baronesse is strap-shaped, and the glume hairs of Champion are short while the glume hairs of Baronesse are long.

Further Embodiments of the Invention

This invention is also directed to methods for producing a barley variety by crossing a first parent barley variety with a second parent barley variety, wherein the first or second barley variety is the variety Champion. Therefore, any methods using the barley variety Champion are part of this invention including selfing, backcrosses, hybrid breeding, and crosses to populations. Any plants produced using barley variety Champion as a parent are within the scope of this invention.

Additional methods include, but are not limited to, expression vectors introduced into plant tissues using a direct gene transfer method such as microprojectile-mediated delivery, DNA injection, electroporation and the like. More preferably, expression vectors are introduced into plant tissues by using either microprojectile-mediated delivery with a biolistic device or by using *Agrobacterium*-mediated transformation. Transformed plants obtained with the protoplasm of the invention are intended to be within the scope of this invention.

Further reproduction of the barley variety Champion can occur by tissue culture and regeneration. Tissue culture of various tissues of barley and regeneration of plants therefrom is well known and widely published. Thus, another aspect of this invention is to provide cells which upon growth and differentiation produce barley plants capable of having the physiological and morphological characteristics of barley variety Champion.

As used herein, the term plant parts includes plant protoplasts, plant cell tissue cultures from which barley plants can be regenerated, plant calli, plant clumps, and plant cells that are intact in plants or parts of plants, such as embryos, pollen, ovules, pericarp, seed, flowers, florets, heads, spikes, leaves, roots, root tips, anthers, pistils and the like.

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. Any DNA sequences, whether from a different species or from the same species that are inserted into the genome using transformation are referred to herein collectively as "transgenes". Over the last fifteen to twenty years several methods for producing transgenic plants have been developed, and the present invention, in particular embodiments, also relates to transformed versions of the barley variety Champion.

Numerous methods for plant transformation have been developed, including biological and physical plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

The most prevalent types of plant transformation involve the construction of an expression vector. Such a vector comprises a DNA sequence that contains a gene under the control of or operatively linked to a regulatory element, for example a promoter. The vector may contain one or more genes and one or more regulatory elements.

A genetic trait which has been engineered into a particular barley plant using transformation techniques could be moved into another line using traditional breeding techniques that are well known in the plant breeding arts. For example, a backcrossing approach could be used to move a transgene from a transformed barley plant to an elite barley variety and the resulting progeny would comprise a transgene. As used herein, "crossing" can refer to a simple X by Y cross, or the process of backcrossing, depending on the context. The term "breeding cross" excludes the processes of selfing or sibbing.

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114: 92-6 (1981).

According to a preferred embodiment, the transgenic plant provided for commercial production of foreign protein is a barley plant. In another preferred embodiment, the biomass of interest is seed. A genetic map can be generated, primarily via conventional RFLP, PCR, and SSR analysis, which identifies the approximate chromosomal location of the integrated DNA molecule. For exemplary methodologies in this regard, see Glick and Thompson, in *Methods in Plant Molecular Biology and Biotechnology* 269-284 (CRC Press, Boca Raton, 1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Various genetic elements can be introduced into the plant genome using transformation. These elements include but are not limited to genes, coding sequences, inducible, constitutive, and tissue specific promoters, enhancing sequences and signal and targeting sequences.

Likewise, by means of the present invention, agronomic genes can be expressed in transformed plants. More particularly, plants can be genetically engineered to express various phenotypes of agronomic interest. Through the transformation of barley the expression of genes can be modulated to enhance disease resistance, insect resistance, herbicide resistance, water stress tolerance and agronomic traits as well as grain quality traits. Transformation can also be used to insert DNA sequences which control or help control male-sterility. DNA sequences native to barley as well as non-native DNA sequences can be transformed into barley and used to modulate levels of native or non-native proteins. Anti-sense technology, various promoters, targeting sequences, enhancing sequences, and other DNA sequences can be inserted into the barley genome for the purpose of modulating the expression of proteins. Exemplary genes implicated in this regard include, but are not limited to, those categorized below.

1. Genes that Confer Resistance to Pests or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., *Science* 266: 789 (1994) (cloning of the tomato Cf-9 gene for resistance to *Cladosporium fulvum*); Martin et al., Science 262: 1432 (1993) (tomato Pto gene for resistance to *Pseudomonas syringae* pv. tomato encodes a protein kinase); Mindrinos et al., *Cell* 78: 1089 (1994) (Arabidopsis RSP2 gene for resistance to *Pseudomonas syringae*); McDowell & Woffenden, (2003) *Trends Biotechnol.* 21(4): 178-83 and Toyoda et al., (2002) *Transgenic Res.* 11 (6):567-82.

*Fusarium* head blight along with deoxynivalenol both produced by the pathogen *Fusarium graminearum* Schwabe have caused devastating losses in barley production. Genes expressing proteins with antifungal action can be used as transgenes to prevent *Fusarium* head blight. Various classes of proteins have been identified. Examples include endochitinases, exochitinases, glucanases, thionins, thaumatin-like proteins, osmotins, ribosome inactivating proteins, flavonoids, and lactoferricin. During infection with *Fusarium graminearum* deoxynivalenol is produced. There is evidence that production of deoxynivalenol increases the virulence of the disease. Genes with properties for detoxification of deoxynivalenol (Adam and Lemmens, In *International Congress on Molecular Plant-Microbe Interactions,* 1996; McCormick et al. *Appl. Environ. Micro.* 65:5252-5256, 1999) have been engineered for use in barley. A synthetic peptide that competes with deoxynivalenol has been identified (Yuan et al., *Appl. Environ. Micro.* 65:3279-3286 (1999)). Changing the ribosomes of the host so that they have reduced affinity for deoxynivalenol has also been used to reduce the virulence of *

Genes used to help reduce *Fusarium* head blight include but are not limited to Tri101(*Fusarium*), PDR5 (yeast), tip-1 (oat), tlp-2(oat), leaftip-1 (wheat), tip (rice), tip-4 (oat), endochitinase, exochitinase, glucanase (*Fusarium*), permatin (oat), seed hordothionin (barley), alpha-thionin (wheat), acid glucanase (alfalfa), chitinase (barley and rice), class beta II-1,3-glucanase (barley), PR5/tip (Arabidopsis), zeamatin (maize), type 1 RIP (barley), NPR1 (Arabidopsis), lactoferrin (mammal), oxalyl-CoA-decarboxylase (bacterium), IAP (baculovirus), ced-9 (*C. elegans*), and glucanase (rice and barley).

(B) A gene conferring resistance to a pest, such as Hessian fly, wheat stem soft fly, cereal leaf beetle, and/or green bug. For example the H9, H10, and H21 genes.

(C) A gene conferring resistance to such diseases as barley rusts, *Septoria tritici, Septoria nodorum*, powdery mildew, *Helminthosporium* diseases, smuts, bunts, *Fusarium* diseases, bacterial diseases, and viral diseases.

(D) A *Bacillus thuringiensis* protein, a derivative thereof or a synthetic polypeptide modeled thereon. See, for example, Geiser et al., *Gene* 48: 109 (1986), who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC Accession Nos. 40098, 67136, 31995 and 31998. Other examples of *Bacillus thuringiensis* transgenes being genetically engineered are given in the following patents and patent applications and hereby are incorporated by reference for this purpose: U.S. Pat. Nos. 5,188,960; 5,689,052; 5,880,275; WO 91/14778; WO 99/31248; WO 01/12731; WO 99/24581; WO 97/40162 and U.S. application Ser. Nos. 10/032,717; 10/414,637; and 10/606,320.

(E) An insect-specific hormone or pheromone such as an ecdysteroid or juvenile hormone, a variant thereof, a mimetic based thereon, or an antagonist or agonist thereof. See, for example, the disclosure by Hammock et al., *Nature* 344: 458 (1990), of baculovirus expression of cloned juvenile hormone esterase, an inactivator of juvenile hormone.

(F) An insect-specific peptide which, upon expression, disrupts the physiology of the affected pest. For example, see the disclosures of Regan, J. *Biol. Chem.* 269: 9 (1994) (expression cloning yields DNA coding for insect diuretic hormone receptor); Pratt et al., *Biochem. Biophys. Res. Comm.* 163: 1243 (1989) (an allostatin is identified in *Diploptera puntata*); Chattopadhyay et al. (2004) *Critical Reviews in Microbiology* 30 (1): 33-54 2004; Zjawiony (2004) *J Nat Prod* 67 (2): 300-310; Carlini & Grossi-de-Sa (2002) *Toxicon*, 40 (11):1515-1539; Ussuf et al. (2001) *Curr Sci.* 80 (7): 847-853; and Vasconcelos & Oliveira (2004) *Toxicon* 44 (4): 385-403. See also U.S. Pat. No. 5,266,317 to Tomalski et al., who disclose genes encoding insect-specific toxins.

(G) An enzyme responsible for a hyperaccumulation of a monoterpene, a sesquiterpene, a steroid, hydroxamic acid, a phenylpropanoid derivative or another non-protein molecule with insecticidal activity.

(H) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23: 691 (1993), who teach the nucleotide sequence of a cDNA encoding tobacco hornworm chitinase, and Kawalleck et al., *Plant Molec. Biol.* 21: 673 (1993), who provide the nucleotide sequence of the parsley ubi4-2 polyubiquitin gene, U.S. application Ser. Nos. 10/389,432, 10/692,367, and U.S. Pat. No. 6,563,020.

(I) A molecule that stimulates signal transduction. For example, see the disclosure by Botella et al., *Plant Molec. Biol.* 24: 757 (1994), of nucleotide sequences for mung bean calmodulin cDNA clones, and Griess et al., *Plant Physiol.* 104: 1467 (1994), who provide the nucleotide sequence of a maize calmodulin cDNA clone.

(J) A hydrophobic moment peptide. See PCT application WO 95/16776 and U.S. Pat. No. 5,580,852 (disclosure of peptide derivatives of Tachyplesin which inhibit fungal plant pathogens) and PCT application WO 95/18855 and U.S. Pat. No. 5,607,914) (teaches synthetic antimicrobial peptides that confer disease resistance).

(K) A membrane permease, a channel former or a channel blocker. For example, see the disclosure by Jaynes et al., *Plant Sci.* 89: 43 (1993), of heterologous expression of a cecropin-beta lytic peptide analog to render transgenic tobacco plants resistant to *Pseudomonas solanacearum.*

(L) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28: 451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(M) An insect-specific antibody or an immunotoxin derived therefrom. Thus, an antibody targeted to a critical metabolic function in the insect gut would inactivate an affected enzyme, killing the insect. Cf. Taylor et al, Abstract #497, *Seventh International Symposium on Molecular Plant-Microbe Interactions* (Edinburgh, Scotland, 1994) (enzymatic inactivation in transgenic tobacco via production of single-chain antibody fragments).

(N) A virus-specific antibody. See, for example, Tavladoraki et al., *Nature* 366: 469 (1993), who show that transgenic plants expressing recombinant antibody genes are protected from virus attack.

(O) A developmental-arrestive protein produced in nature by a pathogen or a parasite. Thus, fungal endo-alpha-1,4-D-polygalacturonases facilitate fungal colonization and plant nutrient release by solubilizing plant cell wall homo-alpha-1,4-D-galacturonase. See Lamb et al., *Bio/Technology* 10: 1436 (1992). The cloning and characterization of a gene which encodes a bean endo-poly-galacturonase-inhibiting protein is described by Toubart et al., *Plant J.* 2: 367 (1992).

(P) A developmental-arrestive protein produced in nature by a plant. For example, Logemann et al., *Bio/Technology* 10: 305 (1992), have shown that transgenic plants expressing the barley ribosome-inactivating gene have an increased resistance to fungal disease.

(Q) Genes involved in the Systemic Acquired Resistance (SAR) Response and/or the pathogenesis-related genes. Briggs, S., *Current Biology,* 5(2):128-131 (1995), Pieterse & Van Loon (2004) *Curr. Opin. Plant Bio.* 7(4):456-64 and Somssich (2003) *Cell* 11 3(7):815-6.

(R) Antifungal genes (Cornelissen and Melchers, *Pl. Physiol.* 101:709-712, (1993) and Parijs et al., *Planta* 183:

258-264, (1991) and Bushnell et al., *Can. J. of Plant Path.* 20(2):137-149 (1998). Also see U.S. application Ser. No. 09/950,933.

(S) Detoxification genes, such as for fumonisin, beauvericin, moniliformin and zearalenone and their structurally related derivatives. For example, see U.S. Pat. No. 5,792,931.

(T) Cystatin and cysteine proteinase inhibitors. See U.S. application Ser. No. 10/947,979.

(U) Defensin genes. See WO 03/000863 and U.S. application Ser. No. 10/178,213.

(V) Genes conferring resistance to nematodes. See WO 03/033651 and Urwin et. al., *Planta* 204:472-479 (1998), Williamson (1999) *Curr Opin Plant Bio.* 2(4):327-31.

2. Genes that Confer Resistance to an Herbicide, for Example:

(A) Acetohydroxy acid synthase, which has been found to make plants that express this enzyme resistant to multiple types of herbicides, has been introduced into a variety of plants (see, e.g., Hattori et al. (1995) *Mol Gen Genet.* 246: 419). Other genes that confer tolerance to herbicides include: a gene encoding a chimeric protein of rat cytochrome P4507A1 and yeast NADPH-cytochrome P450 oxidoreductase (Shiota et al. (1994) *Plant Physiol Plant Physiol* 106:17), genes for glutathione reductase and superoxide dismutase (Aono et al. (1995) *Plant Cell Physiol* 36:1687, and genes for various phosphotransferases (Datta et al. (1992) *Plant Mol Biol* 20:619).

(B) An herbicide that inhibits the growing point or meristem, such as an imidazolinone or a sulfonylurea. Exemplary genes in this category code for mutant ALS and AHAS enzyme as described, for example, by Lee et al., *EMBO J.* 7: 1241 (1988), and Miki et al., *Theor. Appl. Genet.* 80: 449 (1990), respectively. See also, U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270, which are incorporated herein by reference for this purpose.

(C) Glyphosate (resistance imparted by mutant 5-enolpyruvl-3-phosphoshikimate synthase (EPSP) and aroA genes, respectively) and other phosphono compounds such as glufosinate (phosphinothricin acetyl transferase (PAT) and *Streptomyces hygroscopicus* PAT (bar) genes), and pyridinoxy or phenoxy proprionic acids and cycloshexones (ACCase inhibitor-encoding genes). See, for example, U.S. Pat. No. 4,940,835 to Shah et al., which discloses the nucleotide sequence of a form of EPSPS which can confer glyphosate resistance. U.S. Pat. No. 5,627,061 to Barry et al. also describes genes encoding EPSPS enzymes. See also U.S. Pat. Nos. 6,566,587; 6,338,961; 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and U.S. Pat. No. 5,491,288; and international publications EP1173580; WO 01/66704; EP1173581 and EP1173582, which are incorporated herein by reference for this purpose. Glyphosate resistance is also imparted to plants that express a gene that encodes a glyphosate oxido-reductase enzyme as described more fully in U.S. Pat. Nos. 5,776,760 and 5,463,175, which are incorporated herein by reference for this purpose. In addition glyphosate resistance can be imparted to plants by the over-expression of genes encoding glyphosate N-acetyltransferase. See, for example, U.S. application Ser. Nos. 10/462,27, 10/427,692 and 10/427,692. A DNA molecule encoding a mutant aroA gene can be obtained under ATCC accession No. 39256, and the nucleotide sequence of the mutant gene is disclosed in U.S. Pat. No. 4,769,061 to Comai. European Patent Application No. 0 333 033 to Kumada et al. and U.S. Pat. No. 4,975,374 to Goodman et al. disclose nucleotide sequences of glutamine synthetase genes which confer resistance to herbicides such as L-phosphinothricin. The nucleotide sequence of a PAT gene is provided in European Patent No. 0 242 246 and 0 242 236 to Leemans et al. De Greef et al., *Bio/Technology* 7: 61 (1989), describe the production of transgenic plants that express chimeric bar genes coding for PAT activity. See also, U.S. Pat. Nos. 5,969,213; 5,489,520; 5,550,318; 5,874,265; 5,919,675; 5,561,236; 5,648,477; 5,646,024; 6,177,616 B1; and U.S. Pat. No. 5,879,903, which are incorporated herein by reference for this purpose. Exemplary genes conferring resistance to phenoxy proprionic acids and cycloshexones, such as sethoxydim and haloxyfop, are the AccI-S1, AccI-S2 and AccI-S3 genes described by Marshall et al., *Theor. Appl. Genet.* 83: 435 (1992).

(D) An herbicide that inhibits photosynthesis, such as a triazine (psbA and gs+genes) and a benzonitrile (nitrilase gene). Przibilla et al., *Plant Cell* 3: 169 (1991), describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC Accession Nos. 53435, 67441 and 67442. Cloning and expression of DNA coding for a glutathione S-transferase is described by Hayes et al., *Biochem. J.* 285:173 (1992).

(E) Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306 B1; 6,282,837 B1; and 5,767,373; and international publication WO 01/12825.

3. Genes that Confer or Improve Grain Quality, Such as:

(A) Altered fatty acids, for example, by (1) down-regulation of stearyl-ACP desaturase to increase stearic acid content of the plant, by for example, transforming a plant with a nucleic acid encoding an anti-sense of stearyl-ACP desaturase. See Knultzon et al., *Proc. Natl. Acad. Sci. USA* 89: 2624 (1992) and WO99/64579 (Genes for Desaturases to Alter Lipid Profiles in Corn), (2) Elevating oleic acid via FAD-2 gene modification and/or decreasing linolenic acid via FAD-3 gene modification (see U.S. Pat. Nos. 6,063,947; 6,323,392; 6,372,965 and WO 93/11245), [0082] (3) Altering conjugated linolenic or linoleic acid content, such as in WO 01/12800, [0083] (4) Altering LEC1, AGP, Dek1, Superal1, milps, and various Ipa genes such as Ipa1, Ipa3, hpt or hggt. For example, see WO 02/42424, WO 98/22604, WO 03/011015, U.S. Pat. No. 6,423,886, U.S. Pat. No. 6,197,561, U.S. Pat. No. 6,825, 397, US 2003/0079247, US 2003/0204870, WO 02/057439, WO 03/011015 and Rivera-Madrid, R. et al. *Proc. Natl. Acad. Sci.* 92:5620-5624 (1995).

(B) Altered phosphorus content, for example, the (1) Introduction of a phytase-encoding gene would enhance breakdown of phytate, adding more free phosphate to the transformed plant. For example, see Van Hartingsveldt et al., *Gene* 127: 87 (1993), for a disclosure of the nucleotide sequence of an *Aspergillus niger* phytase gene. (2) Up-regulation of a gene that reduces phytate content. In maize for example, this could be accomplished by cloning and then re-introducing DNA associated with one or more of the alleles, such as the LPA alleles, identified in maize mutants characterized by low levels of phytic acid, such as in Raboy et al., *Maydica* 35: 383

(1990) and/or by altering inositol kinase activity as in WO 02/059324, US 2003/0009011, WO 03/027243, US 2003/0079247, WO 99/05298, U.S. Pat. No. 6,197,561, U.S. Pat. No. 6,291,224, U.S. Pat. No. 6,391,348, WO 2002/059324, US 2003/0079247, WO 98/45448, WO 99/55882, WO 01/04147.

(C) Altered carbohydrates effected, for example, by altering a gene for an enzyme that affects the branching pattern of starch or a gene altering thioredoxin (See U.S. Pat. No. 6,531,648). See Shiroza et al., *J. Bacteriol.* 170: 810 (1988) (nucleotide sequence of *Streptococcus mutans* fructosyltransferase gene), Steinmetz et al., *Mol. Gen. Genet.* 200: 220 (1985) (nucleotide sequence of *Bacillus subtilis* levansucrase gene), Pen et al., *Bio/Technology* 10: 292 (1992) (production of transgenic plants that express *Bacillus licheniformis* alpha-amylase), Elliot et al., *Plant Molec. Biol.* 21: 515 (1993) (nucleotide sequences of tomato invertase genes), Sogaard et al., *J. Biol. Chem.* 268: 22480 (1993) (site-directed mutagenesis of barley alpha-amylase gene), and Fisher et al., *Plant Physiol.* 102: 1045 (1993) (maize endosperm starch branching enzyme 11), WO 99/10498 (improved digestibility and/or starch extraction through modification of UDP-D-xylose 4-epimerase, Fragile 1 and 2, Ref1, HCHL, C4H), U.S. Pat. No. 6,232,529 (method of producing high oil seed by modification of starch levels (AGP)). The fatty acid modification genes mentioned above may also be used to affect starch content and/or composition through the interrelationship of the starch and oil pathways.

(D) Altered antioxidant content or composition, such as alteration of tocopherol or tocotrienols. For example, see U.S. Pat. No. 6,787,683, US2004/0034886 and WO 00/68393 involving the manipulation of antioxidant levels through alteration of a phytl prenyl transferase (ppt), WO 03/082899 through alteration of a homogentisate geranyl geranyl transferase (hggt).

(E) Altered essential seed amino acids. For example, see U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO 99/40209 (alteration of amino acid compositions in seeds), WO 99/29882 (methods for altering amino acid content of proteins), U.S. Pat. No. 5,850,016 (alteration of amino acid compositions in seeds), WO 98/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO 98/56935 (plant amino acid biosynthetic enzymes), WO 98/45458 (engineered seed protein having higher percentage of essential amino acids), WO 98/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO 96/01905 (increased threonine), WO 95/15392 (increased lysine), US 2003/0163838, US 2003/0150014, US2004/0068767, U.S. Pat. No. 6,803,498, WO01/79516, and WO 00/09706 (Ces A: cellulose synthase), U.S. Pat. No. 6,194,638 (hemicellulose), U.S. Pat. No. 6,399,859 and US 2004/0025203 (UDPGdH), U.S. Pat. No. 6,194,638 (RGP).

4. Genes that Control Male-Sterility

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. In addition to these methods, Albertsen et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

(A) Introduction of a deacetylase gene under the control of a tapetum-specific promoter and with the application of the chemical N-Ac-PPT (WO 01/29237).

(B) Introduction of various stamen-specific promoters (WO 92/13956, WO 92/13957).

(C) Introduction of the barnase and the barstar gene (Paul et al. *Plant Mol. Biol.* 19:611-622, 1992).

For additional examples of nuclear male and female sterility systems and genes, see also, U.S. Pat. No. 5,859,341; U.S. Pat. No. 6,297,426; U.S. Pat. No. 5,478,369; U.S. Pat. No. 5,824,524; U.S. Pat. No. 5,850,014; and U.S. Pat. No. 6,265,640; all of which are hereby incorporated by reference.

5. Genes that Create a Site for Site Specific DNA Integration.

This includes the introduction of FRT sites that may be used in the FLP/FRT system and/or Lox sites that may be used in the Cre/Loxp system. For example, see Lyznik, et al., Site-Specific Recombination for Genetic Engineering in Plants, *Plant Cell Rep* (2003) 21:925-932 and WO 99/25821, which are hereby incorporated by reference. Other systems that may be used include the Gin recombinase of phage Mu (Maeser et al., 1991; Vicki Chandler, *The Maize Handbook* ch. 118 (Springer-Verlag 1994), the Pin recombinase of *E. coli* (Enomoto et al., 1983), and the R/RS system of the pSRi plasmid (Araki et al., 1992).

6. Genes that Affect Abiotic Stress Resistance (A) These may include but are not limited to flowering, ear and seed development, enhancement of nitrogen utilization efficiency, altered nitrogen responsiveness, drought resistance or tolerance, cold resistance or tolerance, and salt resistance or tolerance and increased yield under stress. For example, see: WO 00/73475 where water use efficiency is altered through alteration of malate; U.S. Pat. No. 5,892,009, U.S. Pat. No. 5,965,705, U.S. Pat. No. 5,929,305, U.S. Pat. No. 5,891,859, U.S. Pat. No. 6,417,428, U.S. Pat. No. 6,664,446, U.S. Pat. No. 6,706,866, U.S. Pat. No. 6,717,034, U.S. Pat. No. 6,801,104, WO2000060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 98/09521, and WO 99/38977 describing genes, including CBF genes and transcription factors effective in mitigating the negative effects of freezing, high salinity, and drought on plants, as well as conferring other positive effects on plant phenotype; US 2004/0148654 and WO 01/36596 where abscisic acid is altered in plants resulting in improved plant phenotype such as increased yield and/or increased tolerance to abiotic stress; WO 2000/006341, WO 04/090143, U.S. application Ser. Nos. 10/817,483 and 09/545,334 where cytokinin expression is modified resulting in plants with increased stress tolerance, such as drought tolerance, and/or increased yield. Also see WO 02/02776, WO 2003/052063, JP2002281975, U.S. Pat. No. 6,084,153, WO 01/64898, U.S. Pat. No. 6,177,275 and U.S. Pat. No. 6,107,547 (enhancement of nitrogen utilization and altered nitrogen responsiveness). For ethylene alteration, see US 20040128719, US 20030166197 and WO 2000/32761. For plant transcription factors or transcriptional regulators of abiotic stress, see e.g. US 2004/0098764 or US 2004/0078852.

(B) Improved tolerance to water stress from drought or high salt water condition. The HVA1 protein belongs to the group 3 LEA proteins that include other members such as wheat pMA2005 (Curry et al., 1991; Curry and Walker-Simmons, 1993), cotton D-7 (Baker et al., 1988), carrot Dc3 (Seffens et al., 1990), and rape pLEA76 (Harada et al., 1989). These proteins are characterized by 11-mer tandem repeats of amino acid domains which may form a probable amphophilic alpha-helical structure that presents a hydrophilic surface with a hydrophobic stripe (Baker et al., 1988; Dure et al., 1988; *Dure*, 1993). The barley HVA1 gene and the wheat pMA2005 gene (Curry et al., 1991; Curry and Walker-Simmons, 1993) are highly similar at both the nucleotide level and predicted amino acid level. These two monocot genes are closely related to the cotton D-7 gene (Baker et al., 1988) and carrot Dc3 gene (Seffens et al., 1990) with which they share a similar structural gene organization (Straub et al., 1994). There is, therefore, a correlation between LEA gene expression or LEA protein accumulation with stress tolerance in a number of plants. For example, in severely dehydrated wheat seedlings, the accumulation of high levels of group 3 LEA proteins was correlated with tissue dehydration tolerance (Ried and Walker-Simmons, 1993). Studies on several Indica varieties of rice showed that the levels of group 2 LEA proteins (also known as dehydrins) and group 3 LEA proteins in roots were significantly higher in salt-tolerant varieties compared with sensitive varieties (Moons et al., 1995). The barley HVA1 gene was transformed into wheat. Transformed wheat plants showed increased tolerance to water stress, (Sivamani, E. et al. *Plant Science* (2000), V.155 pl-9 and U.S. Pat. No. 5,981,842.)

(C) Improved water stress tolerance through increased mannitol levels via the bacterial mannitol-1-phosphate dehydrogenase gene. To produce a plant with a genetic basis for coping with water deficit, Tarczynski et al. (*Proc. Natl. Acad. Sci. USA,* 89, 2600 (1992); WO 92/19731, published No. 12, 1992; *Science,* 259, 508 (1993)) introduced the bacterial mannitol-1-phosphate dehydrogenase gene, mtlD, into tobacco cells via *Agrobacterium*-mediated transformation. Root and leaf tissues from transgenic plants regenerated from these transformed tobacco cells contained up to 100 mM mannitol. Control plants contained no detectable mannitol. To determine whether the transgenic tobacco plants exhibited increased tolerance to water deficit, Tarczynski et al. compared the growth of transgenic plants to that of untransformed control plants in the presence of 250 mM NaCl. After 30 days of exposure to 250 mM NaCl, transgenic plants had decreased weight loss and increased height relative to their untransformed counterparts. The authors concluded that the presence of mannitol in these transformed tobacco plants contributed to water deficit tolerance at the cellular level. See also U.S. Pat. No. 5,780,709 and international publication WO 92/19731 which are incorporated herein by reference for this purpose.

Other genes and transcription factors that affect plant growth and agronomic traits such as yield, flowering, plant growth and/or plant structure, can be introduced or introgressed into plants, see e.g. WO 97/49811 (LHY), WO98/56918 (ESD4), WO97/10339 and U.S. Pat. No. 6,573,430 (TFL), U.S. Pat. No. 6,713,663 (FT), WO 96/14414 (CON), WO 96/38560, WO01/21822 (VRN1), WO 00/44918 (VRN2), WO 99/49064 (GI), WO 00/46358 (FR1), WO 97/29123, U.S. Pat. No. 6,794,560, U.S. Pat. No. 6,307,126 (GAI), WO 99/09174 (D8 and Rht), and WO2004076638 and WO2004031349 (transcription factors).

7. Genes that Confer Agronomic Enhancements, Nutritional Enhancements, or Industrial Enhancements.

Altered enzyme activity for improved disease resistance and/or improved plant or grain quality. For example lipoxygenase levels can be altered to improve disease resistance (Steiner-Lange, S., et al. 2003. *MPMI*. 16(10):893-902. Differential defense reactions in leaf tissues of barley in response to infection by *Rhynchosporium secalis* and to treatment with a fungal avirulence gene product) and/or to improve the quality of the grain resulting in improved flavor for beer, cereal and other food products made from the grain (Douma, A., et al. 2003. U.S. Pat. No. 6,660,915). Another enzyme whose activity can be altered is beta-glucanase for improved plant and/or grain quality (Han, F., et al. 1995. Mapping of beta-glucan content and beta-glucanase activity loci in barley grain and malt. *Theor. Appl. Genet.* 91:921-927; Han, F., et al. 1997. Towards fine structure mapping and tagging major malting quality QTL in barley. *Theor. Appl. Genet.* 95:903-910; Jensen, L. G., et al. 1996. Transgenic barley expressing a protein-engineered, thermostable (1, 3-1, 4)-beta-glucanase during germination. *Proc. Natl. Acad. Sci. U.S.A.* 93(8):3487-3491). Yet another enzyme whose activity can be altered is polyphenol oxidase for improved plant and/or grain quality (Cahoon, R. 2004. U.S. Patent Publication 2004/0214201).

Further embodiments of the invention are the treatment of Champion with a mutagen and the plant produced by mutagenesis of Champion. Information about mutagens and mutagenizing seeds or pollen are presented in the IAEA's *Manual on Mutation Breeding* (IAEA, 1977).

A further embodiment of the invention is a backcross conversion of barley variety Champion. A backcross conversion occurs when DNA sequences are introduced through traditional (non-transformation) breeding techniques, such as backcrossing. DNA sequences, whether naturally occurring or transgenes, may be introduced using these traditional breeding techniques. Desired traits transferred through this process include, but are not limited to nutritional enhancements, industrial enhancements, disease resistance, insect resistance, herbicide resistance, agronomic enhancements, grain quality enhancement, waxy starch, breeding enhancements, seed production enhancements, and male sterility. Descriptions of some of the cytoplasmic male sterility genes, nuclear male sterility genes, chemical hybridizing agents, male fertility restoration genes, and methods of using the aforementioned are discussed in *Hybrid Wheat* by K. A. Lucken (pp. 444-452 In *Wheat and Wheat Improvement*, ed. Heyne, 1987). Examples of genes for other traits include: Leaf rust resistance genes (Lr series such as Lr1, Lr10, Lr21, Lr22, Lr22a, Lr32, Lr37, Lr41, Lr42, and Lr43), *Fusarium* head blight-resistance genes (QFhs.ndsu-3B and QFhs.ndsu-2A), Powdery Mildew resistance genes (Pm21), common bunt resistance genes (Bt-10), and wheat streak mosaic virus resistance gene (Wsml), Russian wheat aphid resistance genes (Dn series such as Dn1, Dn2, Dn4, Dn5), Black stem rust resistance genes (Sr38), Yellow rust resistance genes (Yr series such as Yr1, YrSD, Yrsu, Yr17, Yr15, YrH52), Aluminum tolerance genes (Alt(BH)), dwarf genes (Rht), vernalization genes (Vrn), Hessian fly resistance genes (H9, H10, H21, H29), grain color genes (R/r), glyphosate resistance genes (EPSPS), glufosinate genes (bar, pat) and water stress tolerance genes (Hva1, mtID). The trait of interest is transferred from the donor parent to the recurrent parent, in this case, the barley plant disclosed herein. Single gene traits may result from either the transfer of a dominant allele or a recessive allele. Selection of progeny containing the trait of interest is done by direct selection for a trait associated with a dominant allele. Selection of progeny for a trait that is transferred via a recessive allele requires growing and selfing the first backcross to determine which plants carry the recessive alleles. Recessive traits may require additional progeny testing in successive backcross generations to determine the presence of the gene of interest.

Another embodiment of this invention is a method of developing a backcross conversion Champion barley plant that involves the repeated backcrossing to barley variety Champion. The number of backcrosses made may be 2, 3, 4, 5, 6 or greater, and the specific number of backcrosses used will depend upon the genetics of the donor parent and whether molecular markers are utilized in the backcrossing program. See, for example, von Bothmer, R. et al. 2003. Diversity in Barley (Elsevier Science) and Slafer, G. et al. 2002. *Barley Science: Recent Advances from Molecular Biology to Agronomy of Yield and Quality* (Haworth Press). Using backcrossing methods, one of ordinary skill in the art can develop individual plants and populations of plants that retain at least 70%, 75%, 79%, 80%, 81%, 82%, 83%, 84%, 85%, 86%, 87%, 88%, 89%, 90%, 91%, 92%, 93%, 94%, 95%, 96%, 97%, 98%, or 99% of the genetic profile of barley variety Champion. The percentage of the genetics retained in the backcross conversion may be measured by either pedigree analysis or through the use of genetic techniques such as molecular markers or electrophoresis. In pedigree analysis, on average 50% of the starting germplasm would be passed to the progeny line after one cross to another line, 75% after backcrossing once, 87.5% after backcrossing twice, and so on. Molecular markers could also be used to confirm and/or determine the recurrent parent used. The backcross conversion developed from this method may be similar to Champion for the results listed in Table 1. Such similarity may be measured by a side by side phenotypic comparison, with differences and similarities determined at a 5% significance level. Any such comparison should be made in environmental conditions that account for the trait being transferred. For example, herbicide should not be applied in the phenotypic comparison of herbicide resistant backcross conversion of Champion to Champion.

Another embodiment of the invention is an essentially derived variety of Champion. As determined by the UPOV Convention, essentially derived varieties may be obtained for example by the selection of a natural or induced mutant, or of a somaclonal variant, the selection of a variant individual from plants of the initial variety, backcrossing, or transformation by genetic engineering. An essentially derived variety of Champion is further defined as one whose production requires the repeated use of variety Champion or is predominately derived from variety Champion. International Convention for the Protection of New Varieties of Plants, as amended on Mar. 19, 1991, Chapter V, Article 14, Section 5(c).

This invention also is directed to methods for using barley variety Champion in plant breeding. One such embodiment is the method of crossing barley variety Champion with another variety of barley to form a first generation population of $F_1$ plants. The population of first generation $F_1$ plants produced by this method is also an embodiment of the invention. This first generation population of $F_1$ plants will comprise an essentially complete set of the alleles of barley variety Champion. One of ordinary skill in the art can utilize either breeder books or molecular methods to identify a particular $F_1$ plant produced using barley variety Champion, and any such individual plant is also encompassed by this invention. These embodiments also cover use of transgenic or backcross conversions of barley variety Champion to produce first generation $F_1$ plants.

A method of developing a Champion-progeny barley plant comprising crossing Champion with a second barley plant and performing a breeding method is also an embodiment of the invention. A specific method for producing a line derived from barley variety Champion is as follows. One of ordinary skill in the art would cross barley variety Champion with another variety of barley, such as an elite variety. The $F_1$ seed derived from this cross would be grown to form a homogeneous population. The $F_1$ seed would contain one set of the alleles from variety Champion and one set of the alleles from the other barley variety. The $F_1$ genome would be made-up of 50% variety Champion and 50% of the other elite variety. The $F_1$ seed would be grown and allowed to self, thereby forming $F_2$ seed. On average the $F_2$ seed would have derived 50% of its alleles from variety Champion and 50% from the other barley variety, but various individual plants from the population would have a much greater percentage of their alleles derived from Champion (Wang J. and R. Bernardo, 2000, *Crop Sci.* 40:659-665 and Bernardo, R. and A. L. Kahler, 2001, *Theor. Appl. Genet.* 102:986-992). The $F_2$ seed would be grown and selection of plants would be made based on visual observation and/or measurement of traits. The Champion-derived progeny that exhibit one or more of the desired Champion-derived traits would be selected and each plant would be harvested separately. This $F_3$ seed from each plant would be grown in individual rows and allowed to self. Then selected rows or plants from the rows would be harvested and threshed individually. The selections would again be based on visual observation and/or measurements for desirable traits of the plants, such as one or more of the desirable Champion-derived traits. The process of growing and selection would be repeated any number of times until a homozygous Champion-derived barley plant is obtained. The homozygous Champion-derived barley plant would contain desirable traits derived from barley variety Champion, some of which may not have been expressed by the other original barley variety to which barley variety Champion was crossed and some of which may have been expressed by both barley varieties but now would be at a level equal to or greater than the level expressed in barley variety Champion. The homozygous Champion-derived barley plants would have, on average, 50% of their genes derived from barley variety Champion, but various individual plants from the population would have a much greater percentage of their alleles derived from Champion. The breeding process, of crossing, selfing, and selection may be repeated to produce another population of Champion-derived barley plants with, on average, 25% of their genes derived from barley variety Champion, but various individual plants from the population would have a much greater percentage of their alleles derived from Champion. Another embodiment of the invention is a homozygous Champion-derived barley plant that has received Champion-derived traits.

The previous example can be modified in numerous ways, for instance selection may or may not occur at every selfing generation, selection may occur before or after the actual self-pollination process occurs, or individual selections may be made by harvesting individual spikes, plants, rows or plots at any point during the breeding process described. In addition, double haploid breeding methods may be used at any step in the process. The population of plants produced at each and any generation of selfing is also an embodiment of the invention, and each such population would consist of plants containing approximately 50% of its genes from barley variety Champion, 25% of its genes from barley variety Champion in the second cycle of crossing, selfing, and selection, 12.5% of its genes from barley variety Champion in the third cycle of crossing, selfing, and selection, and so on.

Another embodiment of this invention is the method of obtaining a homozygous Champion-derived barley plant by crossing barley variety Champion with another variety of barley and applying double haploid methods to the $F_1$ seed or $F_1$ plant or to any generation of Champion-derived barley obtained by the selfing of this cross.

Still further, this invention also is directed to methods for producing Champion-derived barley plants by crossing barley variety Champion with a barley plant and growing the progeny seed, and repeating the crossing or selfing along with the growing steps with the Champion-derived barley plant from 1 to 2 times, 1 to 3 times, 1 to 4 times, or 1 to 5 times. Thus, any and all methods using barley variety Champion in breeding are part of this invention, including selfing, pedigree breeding, backcrossing, hybrid production and crosses to populations. Unique starch profiles, molecular marker profiles and/or breeding records can be used by those of ordinary skill in the art to identify the progeny lines or populations derived from these breeding methods.

In addition, this invention also encompasses progeny with the same or greater yield or test weight of Champion, the same or shorter plant height, and the same or greater resistance to smut, stem rust, Septoria, net and spot blotch of Champion. The expression of these traits may be measured by a side by side phenotypic comparison, with differences and similarities determined at a 5% significance level. Any such comparison should be made in the same environmental conditions.

Tables

The present invention, barley cultivar Champion, was compared with currently available barley varieties Baronesse and Camas in Washington State University Statewide Barley Trials from 2004 to 2007 for yield and test weight over numerous different locations. Camas was dropped from the trials in 2006 and 2007. The results are shown in Table 2.

In Table 2, column one shows the year and number of sites, column two shows cultivar, column three shows the yield in bushels per acre (bu/a), column four shows the cultivar ranking for yield (1=highest in trial), column five shows the least significant difference (LSD) statistic for yield, column six shows the test weight in pounds per bushel (lb/bu), column seven shows the cultivars ranking for test weight and column eight shows LSD statistic for test weight. The data shows that Champion had a consistently higher yield and test weight compared to Baronesse and a higher yield compared to Camas.

TABLE 2

| Year/ No. Sites | Cultivar | Yield -bu/a- | Rank | LSD 0.10 | Test Weight -lb/bu- | Rank | LSD 0.10 |
| --- | --- | --- | --- | --- | --- | --- | --- |
| 2004 | Baronesse | 97.3 | 3/32 | 3.4 | 48.3 | 16 | 0.5 |
| 14 | Champion | 101.3 | 1 | | 51.0 | 2 | |
| | Camas | 81.5 | 32 | | 51 | 3 | |

TABLE 2-continued

| Year/ No. Sites | Cultivar | Yield -bu/a- | Rank | LSD 0.10 | Test Weight -lb/bu- | Rank | LSD 0.10 |
| --- | --- | --- | --- | --- | --- | --- | --- |
| 2005 | Baronesse | 84.3 | 3/32 | 4.0 | 49.0 | 17 | 0.5 |
| 12 | Champion | 86.8 | 1 | | 51.0 | 3 | |
| | Camas | 78.0 | 24 | | 50.3 | 4 | |
| 2006 | Baronesse | 94.9 | 10/32 | 3.9 | 50.5 | 21 | 0.4 |
| 12 | Champion | 106.7 | 1 | | 52.8 | 3 | |
| 2007 | Baronesse | 79.8 | 12/26 | 2.8 | 47.9 | 15 | 0.5 |
| 10 | Champion | 91.4 | 1 | | 50.4 | 2 | |
| Average | Baronesse | 89.1 | | | 48.9 | | |
| 48 | Champion | 96.5 | | | 51.3 | | |

The present invention, barley cultivar Champion, was compared with currently available barley varieties Baronesse and Camas in University of Idaho Barley Trials in 2007 for yield and test weight over several different locations. The results are shown in Table 3.

In Table 3, column one shows the region and number of sites within that region, column two shows the cultivar, column three shows the yield in bushels per acre (bu/a), column four shows the cultivar ranking for yield (1=highest in trial), column five shows the LSD statistic for yield, column six shows the test weight in pounds per bushel (lb/bu), column seven shows the cultivar ranking for test weight and column eight shows the LSD statistic for test weight. The data shows that Champion has a consistently higher yield and test weight compared to Baronesse and Camas. These trials tested 14 to 28 different cultivars and Champion was the highest yielding in both regions of Idaho with a relatively high test weight.

TABLE 3

| Region/ No. sites | Cultivar | Yield -bu/a- | Rank | LSD 0.10 | Test Weight -lb/bu- | Rank | LSD 0.10 |
| --- | --- | --- | --- | --- | --- | --- | --- |
| N. Idaho | Baronesse | 74 | 8/14 | 3.0 | 48.2 | 9 | 0.5 |
| 4 | Champion | 85 | 1 | | 51 | 2 | |
| | Camas | 75 | 6 | | 50.4 | 4 | |
| S. Idaho | Baronesse | 124.6 | 9/28 | 7.0 | 51.2 | 16 | 0.7 |
| 5 | Champion | 135.7 | 1 | | 52 | 9 | |
| | Camas | 120 | 12 | | 52 | 10 | |
| Average | Baronesse | 99.3 | | | 49.7 | | |
| 9 | Champion | 110.4 | | | 51.5 | | |
| | Camas | 97.5 | | | 51.2 | | |

The present invention, barley cultivar Champion, was compared with currently available barley cultivar Baronesse in Montana State Agricultural Extension Barley Trials from 2005 to 2007 for yield and test weight over numerous different locations and in both dryland and irrigated trials. The results are shown in Table 4.

In Table 4, column one shows the type of trial and number of sites, column two shows the cultivar, column three shows the yield in bushels per acre (bu/a), column four shows the LSD statistic for yield, column five shows the test weight in pounds per bushel (lb/bu), column six shows the LSD statistic for test weight. The data show that Champion has a statistically higher yield and test weight than Baronesse in Montana.

TABLE 4

| Type/ No. sites | Cultivar | Yield -bu/a- | LSD 0.05 | Test Weight -lb/bu- | LSD 0.05 |
| --- | --- | --- | --- | --- | --- |
| Dryland | Baronesse | 76.2 | 4.4 | 48.7 | 1.0 |
| 13 | Champion | 84.6 | | 51.3 | |

TABLE 4-continued

| Type/<br>No. sites | Cultivar | Yield<br>-bu/a- | LSD<br>0.05 | Test Weight<br>-lb/bu- | LSD 0.05 |
|---|---|---|---|---|---|
| Irrigated | Baronesse | 112.8 | 4.3 | 51.2 | 0.6 |
| 11 | Champion | 119.6 | | 52.8 | |
| Average | Baronesse | 92.9 | 3.1 | 49.9 | 0.6 |
| 24 | Champion | 100.6 | | 52.0 | |

Deposit Information

A deposit of the MONSANTO TECHNOLOGY LLC proprietary Barley Cultivar Champion disclosed above and recited in the appended claims has been made with the American Type Culture Collection (ATCC), 10801 University Boulevard, Manassas, Va. 20110. The date of deposit was Oct. 5, 2010. The deposit of 2,500 seeds was taken from the same deposit maintained by MONSANTO TECHNOLOGY LLC since prior to the filing date of this application. All restrictions will be removed upon granting of a patent, and the deposit is intended to meet all of the requirements of 37 C.F.R. §§1.801-1.809. The ATCC Accession Number is PTA-11385. The deposit will be maintained in the depository for a period of thirty years, or five years after the last request, or for the enforceable life of the patent, whichever is longer, and will be replaced as necessary during that period.

While a number of exemplary aspects and embodiments have been discussed above, those of skill in the art will recognize certain modifications, permutations, additions, and sub-combinations thereof. It is therefore intended that the following appended claims and claims hereafter are interpreted to include all such modifications, permutations, additions, and sub-combinations as are within their true spirit and scope.

What is claimed is:

1. A seed of barley cultivar Champion, representative sample of seed of said cultivar was deposited under ATCC Accession No. PTA-11385.

2. A barley plant, or a part thereof, produced by growing the seed of claim 1.

3. A tissue culture produced from protoplasts or cells from the plant of claim 2, wherein said protoplasts or cells of the tissue culture are produced from a plant part selected from the group consisting of head, awn, leaf, pollen, embryo, cotyledon, hypocotyl, seed, spike, pericarp, meristematic cell, root, root tip, pistil, anther, floret, shoot, stem and callus.

4. A barley plant regenerated from the tissue culture of claim 3, wherein the plant has all of the morphological and physiological characteristics of barley cultivar Champion.

5. A method for producing a barley seed comprising crossing two barley plants and harvesting the resultant barley seed, wherein at least one barley plant is the barley plant of claim 2.

6. A barley seed produced by the method of claim 5.

7. A barley plant, or a part thereof, produced by growing said seed of claim 6.

8. A method of producing an herbicide resistant barley plant wherein the method comprises transforming the barley plant of claim 2 with a transgene wherein the transgene confers resistance to an herbicide selected from the group consisting of imidazolinone, sulfonylurea, glyphosate, glufosinate, phenoxy proprionic acid, cyclohexone, L-phosphinothricin, triazine and benzonitrile.

9. An herbicide resistant barley plant produced by the method of claim 8.

10. A method of producing a pest or insect resistant barley plant wherein the method comprises transforming the barley plant of claim 2 with a transgene that confers pest or insect resistance.

11. A pest or insect resistant barley plant produced by the method of claim 10.

12. The barley plant of claim 11, wherein the transgene encodes a *Bacillus thuringiensis* endotoxin.

13. A method of producing a disease resistant barley plant wherein the method comprises transforming the barley plant of claim 2 with a transgene that confers disease resistance.

14. A disease resistant barley plant produced by the method of claim 13.

15. A method of producing a barley plant with modified fatty acid metabolism, modified carbohydrate metabolism or modified protein metabolism wherein the method comprises transforming the barley plant of claim 2 with a transgene encoding a protein selected from the group consisting of modified glutenins, gliadins, phytase, lipoxygenase, beta-glucanase, polyphenol oxidase, fructosyltransferase, levan-sucrase, α-amylase, invertase and starch branching enzyme or encoding an antisense of stearyl-ACP desaturase.

16. A barley plant having modified fatty acid metabolism, modified carbohydrate metabolism or modified protein metabolism produced by the method of claim 15.

17. A method of introducing a desired trait into barley cultivar Champion wherein the method comprises:
  (a) crossing a Champion plant, wherein a representative sample of seed was deposited under ATCC Accession No. PTA-11385, with a plant of another barley cultivar that comprises a desired trait to produce progeny plants wherein the desired trait is selected from the group consisting of male sterility, herbicide resistance, insect resistance, modified fatty acid metabolism, modified carbohydrate metabolism, modified phytic acid metabolism, modified waxy starch content, modified protein content, improved tolerance to water stress and resistance to bacterial disease, fungal disease or viral disease;
  (b) selecting one or more progeny plants that have the desired trait to produce selected progeny plants;
  (c) crossing the selected progeny plants with the Champion plants to produce backcross progeny plants;
  (d) selecting for backcross progeny plants that have the desired trait and all of the physiological and morphological characteristics of barley cultivar Champion listed in Table 1 to produce selected backcross progeny plants; and
  (e) repeating steps (c) and (d) three or more times in succession to produce selected fourth or higher backcross progeny plants that comprise the desired trait and all of the physiological and morphological characteristics of barley cultivar Champion listed in Table 1.

18. A barley plant produced by the method of claim 17, wherein the plant has the desired trait and all of the physiological and morphological characteristics of barley cultivar Champion.

19. The barley plant of claim 18, wherein the desired trait is herbicide resistance and the resistance is conferred to an herbicide selected from the group consisting of imidazolinone, sulfonylurea, glyphosate, glufosinate, phenoxy proprionic acid, cyclohexone, L-phosphinothricin, triazine and benzonitrile.

20. The barley plant of claim 18, wherein the desired trait is insect resistance and the insect resistance is conferred by a transgene encoding a *Bacillus thuringiensis* endotoxin.

21. The barley plant of claim 18, wherein the desired trait is modified fatty acid metabolism, modified carbohydrate metabolism or modified protein metabolism and said desired trait is conferred by a nucleic acid encoding a protein selected from the group consisting of modified glutenins, gliadins, phytase, lipoxygenase, beta-glucanase, polyphenol oxidase, fructosyltransferase, levansucrase, α-amylase, invertase and starch branching enzyme or encoding an antisense of stearyl-ACP desaturase.

22. The barley plant of claim 20, wherein the desired trait is male sterility and the trait is conferred by a nucleic acid molecule that confers male sterility.

* * * * *